United States Patent
Ermantraut et al.

(10) Patent No.: US 8,278,113 B2
(45) Date of Patent: Oct. 2, 2012

(54) ASSAY DEVICES AND METHODS FOR THE DETECTION OF ANALYTES

(75) Inventors: Eugen Ermantraut, Jena (DE); Torsten Schulz, Jena (DE); Thomas Ellinger, Jena (DE); Daniel Weicherding, Jena (DE)

(73) Assignee: Clondiag GmbH, Jena (DE)

( * ) Notice: Subject to any disclaimer, the term of this patent is extended or adjusted under 35 U.S.C. 154(b) by 466 days.

(21) Appl. No.: 12/385,805

(22) Filed: Jul. 14, 2009

(65) Prior Publication Data
US 2011/0071038 A1    Mar. 24, 2011

Related U.S. Application Data

(63) Continuation of application No. PCT/EP2007/061302, filed on Oct. 22, 2007.

(30) Foreign Application Priority Data

Oct. 20, 2006  (EP) .................................. 06122695

(51) Int. Cl.
*G01N 33/48* (2006.01)

(52) U.S. Cl. ....... 436/165; 436/169; 436/810; 422/68.1; 422/420; 422/430

(58) Field of Classification Search .................. 422/429, 422/430, 68.1; 436/165, 169, 810
See application file for complete search history.

(56) References Cited

U.S. PATENT DOCUMENTS

| 6,168,948 B1 | 1/2001 | Anderson et al. |
| 2005/0009101 A1 | 1/2005 | Blackburn |
| 2006/0160066 A1 | 7/2006 | Bhatia et al. |

FOREIGN PATENT DOCUMENTS

WO    WO 00/12575    3/2000

*Primary Examiner* — Lyle Alexander
(74) *Attorney, Agent, or Firm* — Steptoe & Johnson LLP

(57) ABSTRACT

The present invention relates to devices and methods for performing assays, especially for determining the presence and/or amount of one or more analytes. In particular, the invention relates to a device for the detection of analytes, comprising a reversibly compressible matrix located between a first surface and a second surface, wherein the second surface is located opposite to the first surface, and wherein the distance between the first surface and the second surface is variable. The invention also relates to a corresponding method using such a device for the detection of one or more species of analytes.

17 Claims, 6 Drawing Sheets

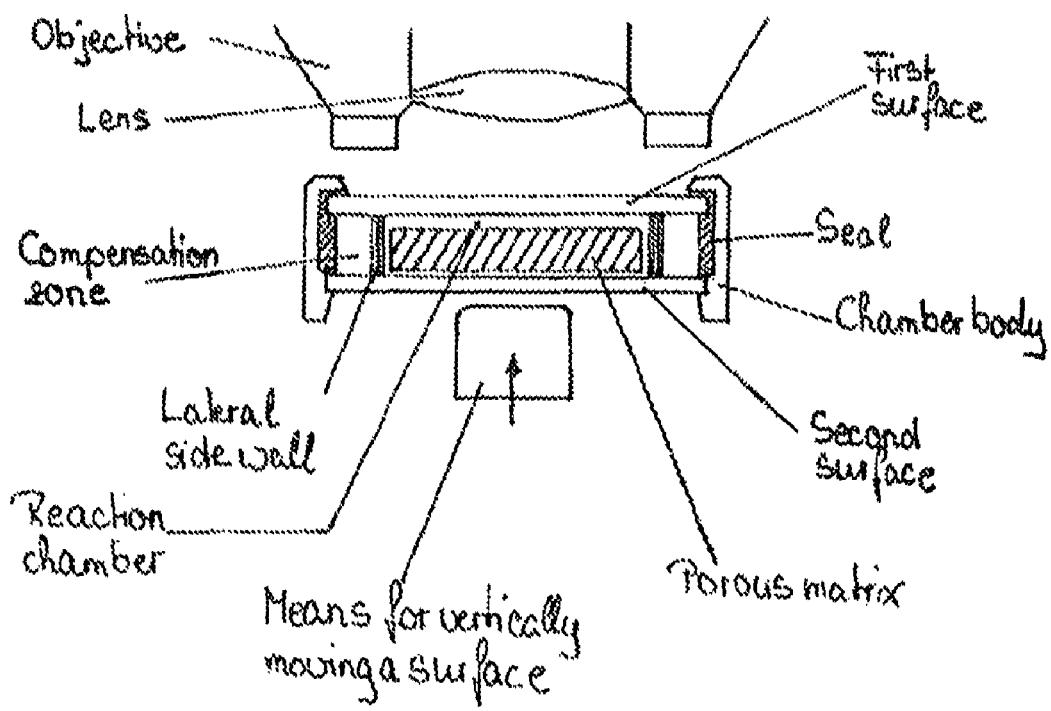

Detection

FIG. 3
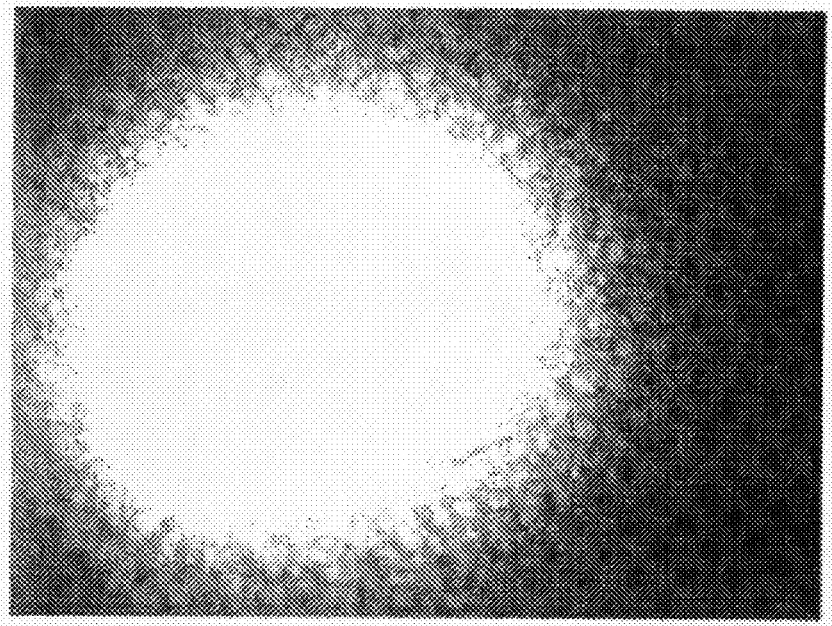
A
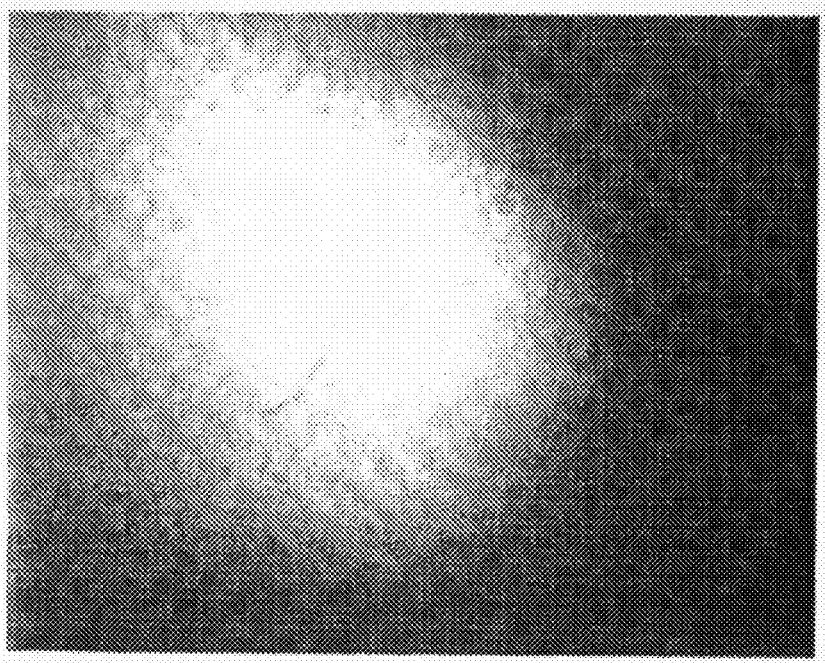
B

ASSAY DEVICES AND METHODS FOR THE DETECTION OF ANALYTES

CLAIM OF PRIORITY

This application claims priority under 35 USC 120 to International Application No. PCT/EP2007/061302, filed on Oct. 22, 2007, which claims priority to European Application Serial No. 06122695.7, filed Oct. 20, 2006, each of which is incorporated by reference in its entirety.

FIELD OF THE INVENTION

The present invention relates to assay devices as well as assays using the same.

BACKGROUND

Assays can be performed to determine the presence and/or the amount of one or more compounds of interest (e.g., analytes). Some assays can determine the presence of multiple analytes. Such assays can be performed using an array of multiple different compounds (e.g., DNA fragments) positioned at specific locations on a surface. The compound at each position interacts with different respective analyte. In use, the array is contacted with a sample containing one or more analytes. The interaction between the compound at each position and the analytes can be detected (e.g., via an optical label) and is indicative of the presence of a particular analyte.

SUMMARY

In one aspect, the invention relates to a device for the qualitative and/or quantitative detection of analytes, comprising a reaction chamber formed within a chamber body between a first surface and a second surface, wherein the second surface is located opposite to the first surface, and wherein the distance between the first surface and the second surface is variable; and a porous matrix located in the reaction chamber between the first surface and the second surface, wherein the matrix is reversibly compressible. The device may further comprise a detection system, preferably an optical detection system, for determining the presence and/or amount of one or more analytes.

The device may further comprise one or more species of capture molecules which are immobilized on the porous matrix, preferably in a site-directed manner.

In one embodiment of the invention, the porous matrix has a porosity of at least 80%. In another embodiment, the porous matrix is swellable when in contact with liquids. In preferred embodiments, the matrix is selected from the group consisting of natural and manufactured sponges, polyvinyl alcohol, and natural and composition rubbers.

At least a part of the first surface and/or the second surface of the device may be made of an elastically deformable material. Optionally, such a material may be optically transparent.

In another embodiment, the device further comprises one or more means, which, when the distance between the first surface and the second surface is reduced, allow keeping the volume of the reaction chamber constant. Such a reduction of the distance between the first surface and the second surface may be accomplished by one or more means allowing the essentially vertical movement of the first surface and/or the second surface relative to each other.

In a further aspect, the invention relates to a method for the qualitative and/or quantitative detection of analytes, comprising introducing a sample supposed to comprise one or more species of analytes to be detected into the reaction chamber of an inventive device, incubating the sample in the reaction chamber; and detecting one or more species of analytes.

In one embodiment, the method further comprises immobilizing one or more species of capture molecules on the porous matrix before incubating the sample in the reaction chamber. This may be accomplished by applying a vectored vacuum perpendicular to the first surface allowing the vertical diffusion of one or more species of capture molecules relative to the first surface.

In another embodiment, the method further comprises introducing one or more agents comprising one or more detectable moieties into the reaction chamber of the device which may have binding affinity for one or more analytes to be detected.

In one embodiment, the molecular interaction formed between the one or more agents comprising one or more detectable moieties and the one or more analytes are detected.

In further embodiments of the invention, the distance between the first surface and the second surface is varied at least in a part of the surface area while incubating the sample in the reaction chamber. Preferably, the distance is reduced, thus giving rise to a displacement of the sample from the reaction chamber. Particularly preferably, the sample is substantially displaced from the reaction chamber.

Subsequently, the reduced distance between the first surface and the second surface may be re-increased. In a further embodiment, the subsequent reduction and re-increase of the distance between the first surface and the second surface is repeated at least twice.

Detection of the one or more analytes may be performed after the distance between the first surface and the second surface has been reduced, i.e. in the compressed state of the device. During the course of the assay detection may be performed once or repeatedly.

In a further aspect, the invention relates to a method for determining the presence of an analyte. The method includes forming a composition of matter including a liquid, an analyte, and a compressible medium comprising a surface capable of capturing the analyte. The surface capable of capturing the analyte occupies a total volume. At least some of the analyte is captured with respect to the surface. The total volume occupied by the surface is decreased and, with the surface in the decreased-total volume state, the presence of the captured analyte is determined.

The composition can further include a detectable label capable of forming a complex with the analyte and the step of determining the presence of the captured analyte can include determining the presence of captured analyte-detectable label complexes.

In another embodiment, the method includes contacting a set of capture sites including multiple capture sites with a mixture including an analyte. Typically, the multiple capture sites are disposed in three dimensions and together occupy a total volume. Each of the capture sites is capable of capturing the analyte. At least some of the analyte is captured with respect to each of some of the capture sites. The total volume occupied by the multiple capture sites is decreased, and, with the multiple capture sites in the decreased volume state, the presence of the captured analyte is determined.

The mixture can further include a detectable label capable of forming a complex with the analyte and the step of determining the presence of the captured analyte can include determining the presence of captured analyte-detectable label complexes.

In another embodiment, the method includes forming a composition of matter including a liquid, an analyte, a detectable label capable including the analyte or an analogue thereof, and a compressible medium including a surface capable of competitively capturing the analyte and the detectable label. The surface occupies a total volume. The total volume occupied by the surface is decreased, and, with the surface in the decreased-total volume state, the presence of the captured detectable label is determined. The presence of the analyte can be determined based on the presence of the captured detectable label.

In another embodiment, the method includes contacting a set of capture sites including multiple capture sites with a mixture including a detectable label and an analyte. The multiple capture sites are disposed in three dimensions and together occupy a total volume. Each of the capture sites is capable of capturing the detectable label in the presence of the analyte. At least some of the detectable label is captured with respect to each of some of the capture sites. The total volume occupied by the multiple capture sites is decreased, and, with the multiple capture sites in the decreased volume state, the presence of the captured detectable label is determined. The presence of the analyte can be determined based on the presence of the captured detectable label.

In another embodiment, the method includes forming a composition of matter including a liquid, an analyte, a detectable label capable of forming a complex including the analyte, and a compressible medium comprising a surface capable of capturing the detectable label in the presence of the analyte. The surface occupies a total volume. At least some of the detectable label is captured with respect to the surface. The total volume occupied by the surface is decreased, and, with the surface in the decreased-total volume state, the presence of the captured detectable label is determined. The presence of the analyte can be determined based on the presence of the captured detectable label.

In another aspect, the invention relates to a device including a support member including a set of capture sites including multiple capture sites. The multiple capture sites are disposed in three dimensions about the member and together occupy a total volume. Each of the capture sites is capable of capturing a common analyte. The support member is configured to accommodate a liquid mixture including an analyte in contact with the capture sites. The device also includes an actuator configured to decrease the total volume occupied by the capture sites, and a detector configured to determine the presence of captured analyte when the capture sites are in the decreased-volume state.

The support member can be configured to accommodate a mixture further including a detectable label capable of forming a complex with the analyte and the detector can be configured to determine the presence of captured analyte based on a determination of captured analyte-detectable label complexes.

BRIEF DESCRIPTION OF THE FIGURES

FIG. 1 is a schematic cross-sectional view of an assay device according to the present invention.

FIG. 2B (b2) illustrates the assay device of FIG. 2B (B1), the capture sites of each set occupying a decreased total volume as compared to FIG. 2B (B2).

FIG. 3 (A-B) illustrates fluorescence of streptavidin-cyanine 5 conjugate immobilized with respect to a polyvinyl acetate (PVA) matrix.

DETAILED DESCRIPTION

Figure 2A:
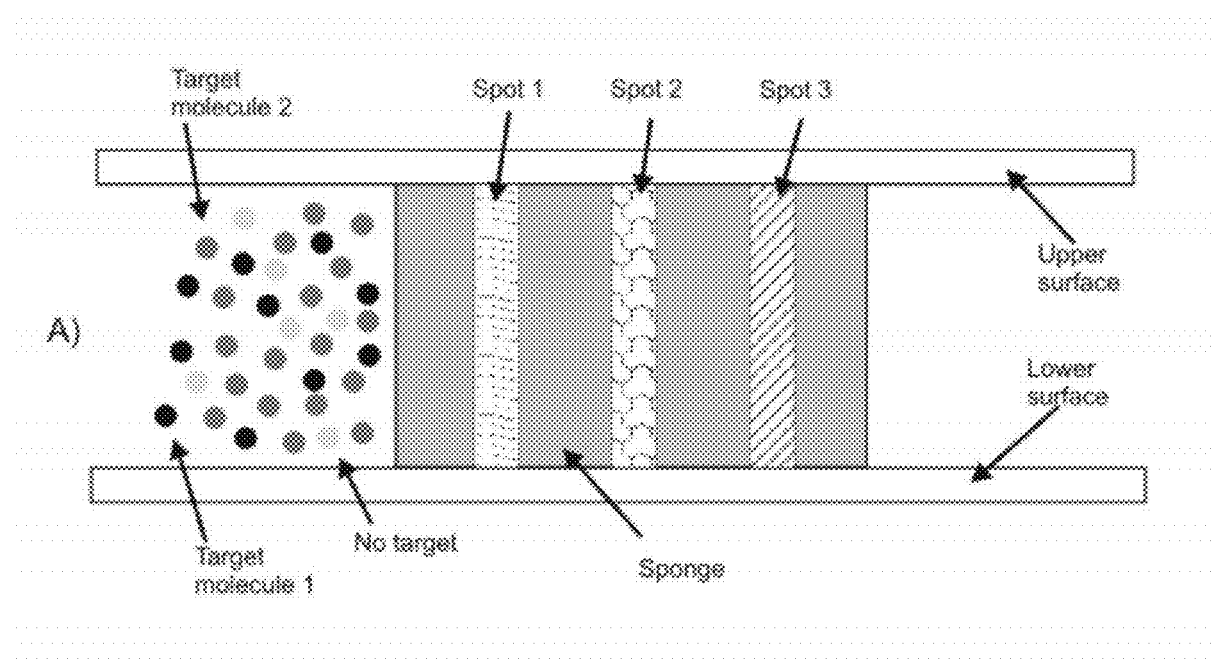
FIG. 2A is a cross sectional view of an assay device having multiple sets of capture sites each occupying a total volume, and the capture sites of each set being capable of capturing an analyte.

In a first aspect, the present invention relates to a device for the qualitative and/or quantitative detection of analytes, comprising:
(a) a reaction chamber formed between a first surface and a second surface, wherein the second surface is located opposite to the first surface, and wherein the distance between the first surface and the second surface is variable; and
(b) a porous matrix located in the reaction chamber between the first surface and the second surface, wherein the matrix is reversibly compressible.

Within the scope of the present invention, a "reaction chamber" (herein also referred to as "reaction space" or "detection chamber" or "chamber") denotes the space formed within a chamber body between a first surface and a second surface. The reaction chamber is laterally limited by sidewalls. The second surface is located opposite to the first surface. Preferably, the first surface and the second surface are arranged in parallel or substantially parallel to each other.

The distance between the first surface and the second surface in the uncompressed state is defined as the distance between the side of the first surface of the device facing the reaction chamber and the side of the second surface facing the reaction chamber and is also referred to as thickness of the reaction chamber. According to the present invention, the thickness of the reaction chamber is usually at most 1 cm, preferably at most 5 mm, particularly preferably at most 3 mm and most preferably at most 1 mm.

In some embodiments of the invention the reaction chamber is designed as a capillary gap, which can be filled by means of capillary forces acting between the first and second surfaces. Usually, a capillary gap has a thickness of at most 1 mm, preferably of at most 750 µm and particularly preferably of at most 500 µm. In preferred embodiments of the invention, the capillary gap has a thickness of 300 µm, with a thickness of 200 µm being more preferred, and a thickness of 150 µm being particularly preferred.

In assay devices according to the present invention the distance between the first surface and the second surface is variable. In preferred embodiments, the distance is variable in a range of 0 mm to 1 mm. Further preferred lower limits for the distance between the first surface and the second surface are in the range of 50 µm to 200 µm. Further preferred upper limits are in the range of 0.3 mm to 0.5 mm.

A porous matrix, as used herein, refers to a porous substrate or a porous composition of substrates, preferably made of one or more reticulate or polymeric materials, that is reversibly compressible. The term "reticulate or polymeric material", as used herein, denotes any material having a fabric- or texture-like structure that can be used for the manufacture of a porous matrix of the invention. The term "reversibly compressible" denotes the property of such a porous matrix to restore, after having been compressed, either completely or for the most part its original volume, i.e. the total volume it has in the uncompressed state. Preferred matrices according to the invention restore after having been fully compressed, at least 50% of its original volume, more preferred matrices restore at least 80% of its original volume, and particularly preferred matrixes restore at least 90% of its original volume. Preferably, the matrices restore their original volume within 30 seconds, more preferably within 15 seconds, and most preferably within 5 seconds after having been fully compressed.

Alternatively, the reversible compressibility of a porous matrix according to the present invention can also be characterized by determining its so-called Shore hardness, which is a measure of the hardness of a material in terms of its elasticity, in particular of its resistance to indentation. The determination of the Shore hardness is the preferred method for analyzing the hardness of rubbers/elastomers, but which is also commonly used for 'softer' plastics such as polyolefins, fluoropolymers, and vinyls. This test provides empirical hardness values that do not correlate to other properties or fundamental characteristics of the material. If no indentation occurs, a value of 100 is obtained, whereas in case of complete indentation a reading a value of 0 is obtained. Preferred matrices according to the present invention show values in the range of 0.01 to 30, and particularly preferred matrices in the range of 0.1 to 20.

In some embodiments of the invention, the porous matrix is attached to the first surface and/or the second surface. Attachment can be achieved either by covalent or non-covalent bonding between the matrix and the respective surface(s). The term "covalent bonding" refers to an intramolecular form of chemical bonding characterized by the sharing of one or more pairs of electrons between two components, producing a mutual attraction that holds the resultant molecule together. The term "non-covalent bonding" refers to a variety of interactions, that are not covalent in nature, between molecules or parts of molecules that provide force to hold the molecules or parts of molecules together usually in a specific orientation or conformation. Such non-covalent interactions include inter alia ionic bonds, hydrophobic interactions, hydrogen bonds, Van-der-Waals forces, and dipole-dipole bonds.

Within the scope of the present invention, the porous matrix may be attached within the reaction chamber either directly to the first surface and/or the second surface or via a polymeric linker molecule, for example a modified silane layer. Such a polymeric linker can serve for the derivative preparation of the surface and therefore for the attachment of the polymeric matrix. In the case of a covalent bonding, polymers such as silanes are used which have been functionalized or modified by means of reactive functionalities like inter alia epoxides, isocyanate or aldehydes. Furthermore, the person skilled in the art is also familiar with the activation of surfaces by succinimide, and imido esters, for example. In addition, it is also possible to further increase the reactivity of a given functional group, for example by reacting an amino group with phosgene or thiophosgene in order to obtain an isocyanate or an isothiocyanate, respectively. Furthermore, it is possible to increase the reactivity of an amino group by reacting it with trichloro-S-triazine, bisepoxide, bisalkylhalide, glutaraldehyde, disuccinimidyl derivatives or heterobifunctional linkers such as 4-succinimidyl-oxycarbonyl-$\alpha$-methyl-$\alpha$-(2-pyridyldithio)toluene or succinimidyl 4-(N-maleimidomethyl)-cyclohexane-1-carboxylate. On the other hand, the reactivity of a carboxy group can be increased by the addition of coupling reagents, such as carbodiimides, in particular dicyclohexylcarbodiimide, or N,N-carbonylimidazole, or by conversion into N-hydroxysuccinimide derivatives. Finally, the reactivity of a hydroxyl group may be increased by reacting it with bisepoxide, bromcyan or disuccinimidyl carbonate or by conversion into aldehyde groups, for example by oxidation with sodium periodate.

In a device according to the invention, the total volume of the porous matrix, i.e. its overall outer volume, may be identical to or smaller than the total volume of the reaction chamber that is defined by the first surface, the second surface and the lateral sidewalls of the device. This means that in case of volume identity the porous matrix completely fills the reaction chamber provided. In some embodiments of the invention, the total volume of the porous matrix is smaller than the total volume of the reaction chamber. Preferred are inventive devices comprising a porous matrix whose total volume is at least 60% of the total volume of the reaction chamber, with matrices whose total volume is at least 80% of the total volume of the reaction chamber being particularly preferred.

The term "porous", as used herein, denotes a matrix comprising in its interior and/or on its surface one or more internal interconnected pores and/or openings. The one or more internal pores and/or openings may be interconnected. Thereby, the porosity of a material is usually defined as a percentage of the total volume of its voids, i.e. the internal pores and openings, available for fluid transmissions to its overall total volume.

One convenient way to calculate the internal pore space in a material is the "water saturation method". In brief, a known volume of the porous material to be analyzed is incubated with a known volume of water for a defined period of time, for example for a few hours, to ensure that the material is fully saturated with water. Then, the excess (i.e. "unsaturated") water is removed and its volume measured. The volume of the pore space can now be calculated by subtracting the volume of the excess water from the total volume of water originally used for the analysis. The porosity of the matrix is finally determined by calculating the ratio of the volume of the pore space, as measured above, and the total volume of the matrix and by multiplying the result obtained with 100%.

In preferred embodiments of the present invention the device comprises a porous matrix having a porosity of at least 30%, preferably of at least 50%. In particular preferred embodiments of the invention the porosity of the porous matrix is at least 80%.

Alternatively, the pore structure of a material can also be analyzed by mercury porosimetry provided that the material in question is sufficiently rigid to withstand relatively high compressive forces and does not react with mercury. The technique involves the intrusion of mercury, a non-wetting liquid on most substrates, at high pressure into a material through the use of a porosimeter. The pore volume as well as the pore size distribution can be determined as a function of pressure, i.e. the external pressure needed to force the mercury into a pore against the opposing force of its surface tension. A detailed description of this method is given, e.g., in Thompson, A. et al. (1987) *Phys. Rev. Lett.* 58, 29, and in Giesche, H. (2006) *Part. Part. Syst. Charact.* 23, 9-19.

Furthermore, it is also possible to determine the porosity of a materials by (static volume) gas adsorption measurements. The principle of this method is based on the introduction of consecutive known amounts of an adsorbate (i.e. an adsorbable gas) into the sample material starting from high vacuum and increasing step by step the pressure up to the adsorbate saturation pressure. Adsorption of the injected gas by the sample causes the pressure to slowly decrease until an equilibrium pressure is established. The gas uptake can be calculated directly from the equilibrium pressure values but a dead volume calibration has to be performed before or after the measurement by a "blank run" (that is an analysis using an inert gas not adsorbed on the sample in the analytical conditions, most commonly used is helium). The method is further detailed, e.g., in Groen, J. C. et al. (2003) *Micropor. Mesopor. Mater.* 60, 1-10.

In preferred embodiments of the invention, the porous matrix is swellable when in contact with liquids. Suitable liquids include inter alia water, organic solutions, inorganic solutions or human and non-human body fluids such as whole blood, plasma, serum, urine, sputum, saliva or cerebrospinal fluid. The term "swellable", as used herein, refers to the property of such a matrix not to be partially or completely soluble in liquids but to reversibly bind liquid molecules or to reversibly intercalate them into its structure, this uptake of liquid resulting in an increase of the matrix's total volume. When compressing the "swelled" matrix or after applying a vacuum to it, the bound or intercalated liquid molecules are released from the matrix thus restoring, at least substantially, the original volume of the matrix.

In particularly preferred embodiments of the invention the porous matrix is selected from the group consisting of natural and manufactured sponges, polyvinyl alcohol, and natural and composition rubbers.

Examples of suitable natural sponges include members of the class Demospongiae. Particular preferred examples include *Spongia graminea, Spongia matamata, Spongia manipulatus, Spongia officinalis, Coscinoderma matthewsi*, and *Rhopaloides odorabile*, all belonging to the so-called "bath sponges" whose skeleton is composed of a flexible spongin matrix and which do not contain hard spicules.

The term "manufactured sponges", as used herein, refers to any non-naturally occurring sponges or sponge-like structures comprising a reversibly compressible porous matrix that are fabricated from materials other than a spongin matrix. Examples of such manufactured sponges according to the present invention include inter cilia sponges fabricated from one or more materials having a fabric- or texture-like structure such as cellulose, collagen, jute, hemp, and synthetic polymeric fibers or mixtures thereof. Suitable synthetic polymeric fibers include, for example, polyurethane, polyester, and nylon as well as mixtures or combinations thereof. The term "sponge-like structure", as used herein, refers to flexible, reversibly compressible foams and/or durable elastomers such as foam rubber, foam resin or foamed plastics (e.g. foamed polystyrene), which are also within the scope of the present invention.

Natural rubber, as used herein, denotes the rubber extracted of the Para rubber tree (*Hevea brasiliensis*). Composition rubbers (commonly also referred to as synthetic rubbers) according to the invention can be made by polymerization of a variety of monomers including, e.g., isoprene (2-methyl-1, 3-butadiene), 2-chloro-1,3-butadiene, and methylpropene with a small percentage of isoprene for cross-linking. Examples of suitable composition rubbers are, for example, styrene-butadiene rubber, acrylonitrile-butadiene rubber, urethane rubber, polyester rubber, chloroprene rubber, butyl rubber, epichlorohydrin rubber, silicone rubber, and phosphazene rubber.

In further embodiments of the invention, the device further comprises one or more species of capture molecules, which are immobilized on the porous matrix.

The term "capture molecule" (also referred to as "molecular probe"), as used herein, denotes a molecule or a particle that shows a specific binding behaviour and/or a characteristic reactivity, which makes it suitable for the detection of other molecules, i.e. the analytes. Each type of molecule or particle, which can be coupled or adsorbed to and immobilized on a matrix or a solid surface and has a specific affinity for other molecules may be used as capture molecule within the scope of the present invention. In preferred embodiments, the capture molecules are selected from the group consisting of nucleic acids, peptides, protein domains, proteins, carbohydrates, low molecular weight chemical compounds, and analogs and/or mixtures thereof.

However, it is also possible to use naturally occurring or synthetic particles as capture molecules. These particles may be optionally coated with additional binding molecules such as nucleic acids or antibodies that may be specific for one or more species of analytes to be detected. Examples of naturally occurring particles include inter alia prokaryotic cells (e.g. bacterial cells such as *Escherichia coli* or *Bacillus subtilis*), eukaryotic cells (e.g. yeasts such as *Saccharomyces cerevisiae*, insect cells such as Sf9 or High 5 cells, immortalized cell lines such as HeLa or Cos cells, and primary cells such as mammalian blood cells) or viruses (e.g. phage particles such as M13 or T7 phage). Prokaryotic or eukaryotic cells may be grown in cell culture dishes, harvested, and added to the porous matrix of the invention. Alternatively, the cells may also be directly grown in the porous matrix material. Methods for cultivating prokaryotic or eukaryotic cells are well established in the art (see, e.g., Tanner, R. S. (2002) *Cultivation of Bacteria and Fungi*. In: Hurst, C. J. et al., *Manual of Environmental Microbiology*, 9th ed., Blackwell Publishing Ltd., Oxford; Bonifacino, J. S. et al. (2001) *Current Protocols in Cell Biology*, Wiley & Sons, Hoboken, N.J.). Accordingly, in case of using viruses as capture molecules, it is not only possible to add the purified virus preparations to the porous matrix but also to grow the respective viruses' host cells in the matrix material, to infect the same with the viruses within the matrix, and upon release from the host cells to couple the propagated viruses to the matrix material (see, e.g., Waldor, M. et al. (2005) *Phage—Role in Pathogenesis and Biotechnology*. 1st ed., Blackwell Publishing Ltd., Oxford; Clackson, T., and Lowman, H. B. (2004) *Phage Display—A Practical Approach*. 1st ed., Oxford University Press, Oxford). Examples of synthetic particle include inter alia magnetic beads (e.g. paramagnetic polystyrol beads, also known as Dynabeads™) and latex beads.

The term "species", as used herein in connection with capture molecules, refers to a particular type of capture molecule or particle, i.e. a specific nucleic acid molecule or a specific antibody or a specific cell, for example. Accordingly, the term "one or more species" denotes one or more different types of capture molecules such as one or more nucleic acid molecules having different nucleotide sequences or one or more antibodies having different binding affinities or one or more different types of cells. More than one species of capture molecule concomitantly used are also referred to as "library".

The term "library", as used herein, refers to a plurality of different species of capture molecules. Such libraries comprise at least two but may also comprise many more different molecules. Typically, the libraries used in the present invention comprise at least five different species, preferably at least ten different species, more preferably at least 20 different species, and most preferably at least 50 different species.

Examples of nucleic acids that can be used as capture molecules in the present invention include naturally occurring nucleic acids such as deoxyribonucleic acid (DNA) or ribonucleic acid (RNA) as well as nucleic acid analogs such as inter alia peptide nucleic acids (PNA) or locked nucleic acids (LNA). Specific examples of naturally occurring nucleic acids include DNA sequences such as genomic DNA or cDNA molecules as well as RNA sequences such as hnRNA or mRNA molecules or the reverse complement nucleic acid sequences thereof. Such nucleic acids can be of any length and can be either single-stranded or double-stranded molecules. Typically, nucleic acid capture molecules of the invention are 10 to 100 bases in length, preferably of 15 to 50 bases, and particularly preferably of 20 to 30 bases. If the analytes to be detected are nucleic acids as well, the capture molecules are preferably single-stranded nucleic acid molecules, particularly preferably single-stranded nucleic acid molecules having at least one sequence region, which is complementary to a sequence region of the analytes, thus allowing Watson-Crick base-pairing between the capture molecules and the analytes to be detected. In specific embodiments of the invention, such nucleic acid capture molecules may be used as primers in a polymerase chain reaction (PCR) in order to amplify any analyte of interest being present in a given sample.

Peptides, protein domains or proteins that can be used as capture molecules in the present invention comprise naturally occurring as well as artificially designed molecules, for example by means of recombinant DNA technology or via chemical synthesis. Methods for the design and preparation of such proteinaceous molecules are well established in the art (see, for example, Sambrook, J. et al. (1989) *Molecular, Cloning: A Laboratory Manual,* 2nd ed., Cold Spring Harbor Laboratory Press, Cold Spring Harbor, N.Y.). Typically, peptide capture molecules of the invention are 2 to 100 amino acids in length, preferably of 5 to 50 amino acids, and particularly preferably of 10 to 25 amino acids.

The term "protein domain", as used herein, refers to a part of a polypeptide sequence that is defined with regard to the specific function it exhibits, such as ligand binding or catalytic activity. Preferred examples of such protein domains are inter alia Fab-fragments of antibodies, the ligand-binding domains of cellular receptors such as G-protein coupled receptors, receptor tyrosine kinases or nuclear receptors, and the carbohydrate-binding domain of lectins.

Examples of carbohydrates that can be used as capture molecules in the present invention include monosaccharides such as glucose or fructose, disaccharides such as lactose or sucrose, as well as oligosaccharides and polysaccharides such as starch, with monosaccharides being preferred.

The term "low molecular weight chemical compound", as used herein, denotes a molecule, preferably an organic molecule, comprising at least two carbon atoms, but preferably not more than seven carbon bonds, having a molecular weight in the range between 100 and 2,000 Dalton, preferably between 100 and 1,000 Dalton, and optionally including one or two metal atoms. Examples of such molecules include inter alia imidazoles, indoles, isoxazoles, oxazoles, pyridines, pyrimidines, and thiazoles.

The capture molecules are immobilized on the porous matrix in the reaction chamber of the inventive device either directly or via a linker molecule by covalent or non-covalent interactions. Depending on the type of capture molecule and the intended application, in each case a large variety of specific coupling reagents and suitable linker molecules is commercially available from different providers and well established in the art (see, e.g., Sambrook, J. et al., supra; Ausubel, F. M. et al. (2001) *Current Protocols in Molecular Biology*, Wiley & Sons, Hoboken, N.J.; and Lottspeich, F., and Zorbas H. (1998) *Bioanalytik*, Spektrum Akademischer Verlag, Heidelberg/Berlin, Germany).

In preferred embodiments of the invention, the one or more species of capture molecules are immobilized on the matrix in a site-directed manner. The term "in a site-directed manner", as used herein, refers to the fact that a given species of capture molecules is not randomly distributed throughout the porous matrix but spatially restricted to a distinct area of the matrix. In a particularly preferred embodiment, the area, to which the spatial distribution of a given species of capture molecules is restricted, has a substantially column-like shape and passes the porous matrix at least partially in vertical direction relative to the first surface and/or the second surface. As used herein, such an area of the porous matrix is also referred to as "three-dimensional spot". A porous matrix according to the invention comprises typically at least two different three-dimensional spots, preferably at least five or at least ten different three-dimensional spots, more preferably at least 20 different three-dimensional spots, and most preferably at least 50 different three-dimensional spots. Within the scope of the present invention, the distance between two such three-dimensional spots is in the range of 300 µm to 2 mm, with a distance of 500 µm being preferred. Compared to conventional systems in which the capture molecules are typically immobilized on a two-dimensional surface such a "three-dimensional immobilization pattern" provides an increased reaction area for the interaction between a given capture molecule and an analyte to take place. This, in turn, may result in quantitative binding and thus an improved sensitivity of detection.

According to the present invention, the first surface and the second surface can be made of the same material or of different materials. It is also possible that the first surface and/or the second surface comprise(s) surface areas made of different materials, for example, one surface area is made of a transparent material, whereas the remaining surface area is made of a non-transparent material. For example, it may be preferable that the first surface and/or the second surface comprise(s) a central, optionally rectangular, surface area (i.e. a "window") made of transparent material, whereas the remainder of the surface area (i.e. the "border") is made of a non-transparent material.

In preferred embodiments of the invention, at least a part of the first surface and/or the second surface is/are made of an amorphous material. The term "amorphous material", as used herein, refers to a solid in which there is no long-range order of the positions of the atoms, i.e. a non-crystalline material. Examples of such amorphous materials include inter alia ceramic materials such as aluminum oxide ceramics, glasses such as borofloat glasses, silicone, and other synthetic polymers such as polystyrene or polytetrafluorethylene (Teflon™).

In a particularly preferred embodiment of the invention, at least a part of the first surface and/or the second surface is/are made of a transparent material, i.e. a light-permeable material. Examples of suitable transparent materials include inter alia glasses or glass-like materials such as window glass, borofloat glasses, quartz glasses, topaz glass, or sapphire glass, as well as synthetic polymers such as polymethylmethacrylate, polycarbonate, polycarbonate, polystyrene, or acryl.

In another preferred embodiment of the invention, at least a part of the first surface and/or the second surface is/are elastically deformable. That is, at least a part of the respective surface(s) is/are made of an elastically deformable material, for example an elastic membrane. A particularly preferred elastic membrane is made of silicone rubber.

In a further preferred embodiment, the inventive device further comprises a chamber body. The term "chamber body", as used herein, is understood to denote the solid body surrounding the reaction chamber, which is formed by the first surface, the second surface, and the lateral sidewalls.

The first surface, the second surface, and/or one or more of the lateral sidewalls may be integral part(s) of the chamber body. That is, the respective surface(s) being an integral part of the chamber body is/are made of the same material as the chamber body. Alternatively, one or more of the first surface, the second surface, and/or one or more lateral sidewalls, respectively, may be made of another material than the chamber body. Within the scope of the present invention, it is thus possible that all four surfaces defining the reaction chamber are made of the same material, that two or three surfaces are made of the same material, whereas the remaining surface(s) is (are) made of different material(s), or that each surface is made of different materials.

Optionally, the first surface and/or the second surface of the reaction chamber may comprise one or more openings, which may be connected to means such as a vacuum pump that allow the application of a vectored vacuum perpendicular to the first surface. In a preferred embodiment of the invention, the application of such vectored vacuum enables and/or facilitates the vertical diffusion (relative to the first surface) of the one or more species of capture molecules through the porous matrix during immobilization.

In other special embodiments, instead of or in addition to the first surface and the second surface one or more lateral sidewalls delimiting the reaction chamber may comprise one or more openings, which may be connected to means allowing the application of a vectored vacuum, preferentially in parallel to the first surface. A preferred means is a vacuum pump. In a preferred embodiment of the invention, the application of such vectored vacuum enables and/or facilitates the lateral diffusion (relative to the first surface) of the sample through the porous matrix after having been introduced into the reaction chamber. Typically, the vacuum applied to the reaction chamber is in the range of 1 hPa to 1013 hPa, preferably in the range of 10 hPa to 750 hPa, and particularly preferably in the range of 100 hPa to 500 hPa.

The chamber body is preferably made at least in part of an amorphous material, in particular of a transparent material. Suitable materials include inter alia glass, synthetic materials such as polycarbonate (e.g. Macrolon™), nylon, polymethylmethacrylate, and Teflon™, and metals such as high-grade steel, aluminum, and brass. In some embodiments of the invention, the chamber body is made of electrically conductive material, which is preferably selected from the group consisting of polyamide with 5 to 30% carbon fibers, polycarbonate with 5 to 30% carbon fibers, polyamide with 2 to 20% stainless steel fibers, and polyphenylensulfide with 5 to 40% carbon fibers.

It is also within the scope of the present invention that the reaction chamber of the device is not designed as a single reaction space but comprises two or more sub-chambers. This can be achieved by providing the first surface and/or the second surface with one or more partitions or cavities, which serve as lateral sidewalls between the two or more sub-chambers. It is preferred that the lateral sidewalls between the two or more sub-chambers are formed by elastic seals. In special embodiments, the partitions on the first surface and/or the second surface do not span the distance between the first surface and the second surface in the non-operated device, that is before the distance between the first surface and the second surface is varied. Accordingly, in the non-operated device the two or more sub-chambers are in fluidic contact with each other. However, if the distance between the first surface and the second surface is reduced, the sub-chambers can be separated. Thus, by varying the distance between said two surfaces the partitions can be operated like valves.

In another embodiment of the invention, the device further comprises one or more means which allow the essentially vertical movement of the first surface and/or the second surface relative to each other. The term "vertical movement", as used herein, denotes a movement of either one or both surfaces of the device perpendicular to their respective surface areas, thus resulting in a variation of the distance between them. A variation of the distance between said two surfaces is understood to include both a reduction and an increase of said distance. A reduction of the distance between the first surface and the second surface of the device can be achieved either by moving the first surface towards the second surface, by moving the second surface towards the first surface or by moving both surfaces towards each other. Vice versa, an increase of the distance between the first surface and the second surface of the device can be achieved either by moving the first surface away from the second surface, by moving the second surface away from the first surface or by moving both surfaces away from each other. In particular, it is preferred to vary the distance between the first surface and the second surface by applying pressure and/or traction to either one or to both surfaces via said one or more means.

Any means or actuator allowing the vertical movement of the first surface and/or the second surface relative to each other may be suitable for carrying out the invention. Preferably, the one or more means are selected from the group consisting of a rod, a pin, a tappet, and a screw, with a tappet being particularly preferred.

The device according to the present invention may further comprise one or more means, which, when the distance between the first surface and the second surface is reduced, allow keeping the volume of the reaction chamber essentially constant. That is, compensation zones are provided to which any liquid and/or gaseous material being present in the reaction chamber between the first surface and the second surface can be displaced when the distance between said surfaces is reduced.

Preferably, this is accomplished by providing a reaction chamber laterally delimited by sidewalls made of an elastic material. According to the present invention, one or more lateral sidewalls can be made of an elastic material. A particularly preferred elastic material is silicone rubber.

An alternative means, which allows keeping the volume of the reaction chamber essentially constant, may comprise a channel that is connected to the reaction chamber of the device and that is filled with a viscous liquid such as silicon oil. Thus, when the distance between the first surface and the second surface is reduced, the viscous liquid becomes displaced in the channel by the excess sample material becoming displaced from the reaction chamber.

In another preferred embodiment, the device according to the present invention further comprises a temperature control unit and/or temperature regulating unit for controlling and/or regulating the temperature within the reaction chamber, for example, in order to achieve optimal reaction conditions for the formation of a complex between the capture molecules and the analytes of interest to occur with high sensitivity and specificity. Furthermore, in case the analytes to be detected are nucleic acid molecules, it may also be possible to use the temperature control unit and/or temperature regulating unit of the device for amplifying the number of analytes present in the sample by means of a polymerase chain reaction (PCR) to facilitate further detection. PCR is an established standard method in molecular biology that is described in detail, e.g., in Sambrook et al., supra; and in Ausubel, F. M. et al., supra. Such a temperature control unit and/or temperature regulating unit may comprise one or more separate heating and/or cooling elements, which may directly contact the first surface and/or the second surface. Preferably, the one or more heating and/or cooling elements are preferred to be made of a heat conductive material. Examples of such heat conductive materials include inter alia silicon, ceramic materials like aluminum oxide ceramics, and/or metals like high-grade steel, aluminum, copper, or brass. An exemplary detailed description of a temperature control unit and/or temperature regulating unit according to the present invention can also be found in the International Patent Application WO 01/02094, whose relevant contents are herewith explicitly referred to.

In a preferred embodiment, controlling/regulating the temperature within the reaction chamber is achieved by using a chamber body made of an electrically conductive material. Preferred examples of electrically conductive materials include electrically conductive synthetic materials, such as polyamide with 5 to 30% carbon fibers, polycarbonate with 5 to 30% carbon fibers, polyamide with 2 to 20% stainless steel fibers, and polyphenylene sulfide with 5 to 40% carbon fibers. It is further preferred that the chamber body is designed to comprise swellings and diminutions which allow specific heating of the reaction chamber or the corresponding surfaces. Furthermore, the use of such elements has the advantage that, even when using a material with a comparably low heat conductivity, a homogenous tempering of the reaction chamber is ensured, as heat is released in each such volume element.

Measuring the temperature in the reaction space can be performed by various methods well established in the art, for example by using integrated resistance sensors, semi-conductor sensors, light waveguide sensors, polychromatic dyes or liquid crystals. Furthermore, the temperature in the reaction chamber can be determined by using an integrated temperature sensor in the chamber body, a pyrometer or an infrared sensor, or by measuring the temperature-dependent alteration of parameters such as the refraction index at the surface on which detection takes place or the pH value of the sample, for example by measuring the color alteration of a pH-sensitive indicator.

In some embodiments of the invention, the device further comprises a detection system connected to the reaction chamber. Preferably, the detection system is positioned opposite to the first surface and/or the second surface, on which detection take(s) place.

The selection of a suitable detection system depends on several parameters such as the nature of the capture molecules used, the optional presence of additional agents (e.g. dyes or labels) used for detection or the kind of analytes to be detected. Various optical and non-optical detection systems are well established in the art. A general description of detection systems that can be used with the invention can be found, for example, in Lottspeich, F., and Zorbas H., supra, in particular chapters 23.3 and 23.4.

In preferred embodiments of the invention, the detection system is an optical detection system, in particular a fluorescence-optical detection system. In general, performing the method according to the present invention involves the use of rather simple detection systems based on the measurement of parameters such as fluorescence, optical absorption, resonance transfer, and the like. Preferred systems for the detection of molecular interactions are based on the comparison of the fluorescence intensities of spectrally excited analytes labeled with fluorophores. Fluorescence is the capacity of particular molecules to emit their own light when excited by light of a particular wavelength resulting in a characteristic absorption and emission behavior. In particular, quantitative detection of fluorescence signals is performed by means of modified methods of classical fluorescence microscopy (for review see, e.g., Lichtman, J. W., and Conchello, J. A. (2005) *Nature Methods* 2, 910-919; Zimmermann, T. (2005) *Adv. Biochem. Eng. Biotechnol.* 95, 245-265). Thereby, the signals resulting from light absorption and light emission, respectively, are separated by one or more filters and/or dichroites and imaged on suitable detectors such as two-dimensional CCD arrays. Data analysis is performed by means of digital image processing.

Another optical detection system that may also be used when performing the present invention is confocal fluorescence microscopy, wherein the object is illuminated in the focal plane of the lens via a point light source. Importantly, the point light source, object and point light detector are located on optically conjugated planes. Examples of such confocal systems are described, e.g., in Diaspro, A. (2002) *Confocal and 2-photon-microscopy: Foundations, Applications and Advances*, Wiley-Liss, Hobroken, N.J. The fluorescence-optical system of the present invention is particularly preferred to represent a fluorescence microscope without an autofocus, for example a fluorescence microscope having a fixed focus.

In alternative devices according to the present invention means for performing an electrochemical detection of the analytes are provided, for example by measuring the alteration of redox potentials via electrodes connected to the first surface and/or the second surface (see, e.g., Zhu, X. et al. (2004) *Lab Chip.* 4, 581-587) or by cyclic voltometry (sec, e.g., Liu, J. et al. (2005) *Anal. Chem.* 77, 2756-2761; and Wang, J. (2003) *Anal. Chem.* 75, 3941-3945). Furthermore, it is also possible to provide means for performing an electric detection, for example by impedance measurement (see, e.g., Radke, S. M. et al. (2005) *Biosens. Bioelectron.* 20, 1662-1667).

In a further aspect, the present invention provides a method for the qualitative and/or quantitative detection of analytes, comprising:
(a) introducing a sample supposed to comprise one or more species of analytes to be detected into the reaction chamber of a device as defined in the present invention;
(b) incubating the sample in the reaction chamber; and
(c) detecting one or more species of analytes.

The term "sample", as used herein, refers to a liquid or a gaseous material which is to be analyzed by using a device according to the present invention, and which is supposed to comprise one or more species of analytes to be detected. Preferably, the sample to be analyzed is a biological sample. Examples of liquid samples that can be analyzed using the invention include inter alia organic and inorganic chemical solutions, drinking water, sewage, human and non-human body fluids such as whole blood, plasma, serum, urine, sputum, salvia or cerebrospinal fluid, cellular extracts from animals, plants or tissue cultures, prokaryotic and eukaryotic cell suspensions, phage preparations and the like. Examples of suitable gaseous or aerosol samples include inter alia fresh air, respiratory samples (i.e. breath), marsh gas, emissions from motors and other apparatuses and the like. The sample may further comprise one or more additional agents such as diluents, solvents or buffers that may result from an optional purification and/or processing of the sample prior to its introduction into the reaction chamber.

The sample to be analyzed may comprise one or more species of analytes to be detected when performing the present invention. The term "analyte", as used herein, refers to a molecule or particle having a specific binding behaviour and/or a characteristic reactivity, which enables its detection by one or more species of capture molecules, as defined above. Virtually any type of molecule or particle may represent a target molecule within the scope of the present invention. In preferred embodiments, the analytes are selected from the group consisting of nucleic acids, peptides, protein domains, proteins, carbohydrates, low molecular weight chemical compounds, and analogs and/or mixtures thereof.

Particles that may be used as target molecules according to the present invention include naturally occurring as well as synthetic particles, as long as they are capable of binding one or more species of capture molecules, optionally via one or more molecules on their respective surfaces such as cell surface receptors or the like. Examples of naturally occurring particles include inter alia prokaryotic cells (e.g. bacterial cells such as *Escherichia coli* or *Bacillus subtilis*), eukaryotic cells (e.g. *Saccharomyces cerevisiae*, insect cells such as Sf9 or High 5 cells, immortalized cell lines such as HeLa or Cos cells, and primary cells such as mammalian blood cells) or viruses (e.g. phage particles such as M13 or T7 phage). Examples of synthetic particle include inter alia magnetic beads and latex beads, which may optionally be coated with one or more species of molecules or fragments thereof (i.e. a library), in particular one or more species of biological macromolecules such as nucleic acids or proteins.

The term "species", as used herein in connection with analytes, refers to a particular type of target molecule, i.e. a specific nucleic acid molecule or a specific peptide or protein, for example. Accordingly, the term "one or more species" denotes one or more different types of analytes such as one or more nucleic acid molecules having different nucleotide sequences or one or more peptides or proteins differing in their amino acid sequences.

Examples of nucleic acids that can be used as analytes in the present invention include naturally occurring nucleic acids such as DNA or RNA as well as nucleic acid analogs such as inter alia PNA or LNA, as already described in connection with the capture molecules of the invention. Such nucleic acids can be of any length and can be either single-stranded or double-stranded molecules. Typically, nucleic acid analytes of the invention are 10 to 10,000 bases in length, preferably of 20 to 2,000 bases, and particularly preferably of 50 to 150 bases.

Peptides, protein domains or proteins that are suitable as analytes in the present invention comprise naturally occurring as well as artificially designed molecules, as also already described for the capture molecules of the invention. Typically, such proteinaceous analytes of the invention are 5 to 3000 amino acids in length, preferably of 10 to 500 amino acids, and particularly preferably of 20 to 300 amino acids.

Examples of carbohydrates that can be used as analytes in the present invention include monosaccharides such as glucose or fructose, disaccharides such as lactose or sucrose, as well as oligosaccharides and polysaccharides such as starch.

The term "low molecular weight chemical compound", as used herein and already described above, denotes an molecule, preferably an organic molecule, comprising at least two carbon atoms, but preferably not more than seven carbon bonds, having a molecular weight in the range between 100 and 2,000 Dalton, preferably between 100 and 1,000 Dalton, and optionally including one or two metal atoms. Examples of such molecules include inter alia imidazoles, indoles, isoxazoles, oxazoles, pyridines, pyrimidines, and thiazoles.

The sample to be analyzed may be introduced directly into the reaction chamber via one or more openings, which may be lockable and/or sealable, being present in the first surface, the second surface and/or one or more lateral sidewalls. The sample may be transferred, optionally along with additional reagents, into the reaction chamber by using a suitable pressure-generating means, for example, a pipette, a syringe or an automated unit, which may be, for example, a functional unit of a processing apparatus. In preferred embodiments of the invention, the sample is introduced via one or more openings in one or more lateral sidewalls of the reaction chamber, with an introduction via one lateral sidewall being particularly preferred. Alternatively, the sample may also be introduced into the reaction chamber by capillary force without any external manipulation, for example by placing the sample immediately adjacent to one of the openings being present in any of the surfaces defining the reaction chamber.

The method of the present invention is intended to be performed without the requirement to remove and/or replace the sample and/or any other reagents in the reaction chamber during the incubation and/or detection periods, respectively. In particular, no washing or rinsing steps that would require such removal/replacement are necessary, for example in order to improve the signal-to-noise ratio of the detection method used.

However, some applications may require the introduction of additional reagents into the reaction chamber during the incubation and/or detection periods. For example, one or more agents comprising a detectable marker such as labeled binding molecules or enzyme substrates that would otherwise interfere with further detection, for example due to competing binding sites with the capture molecules, may be introduced into the reaction chamber only after the sample has added in order to enable an accurate detection of capture molecule/analyte interactions. Such additional solutions or gases may also be directly introduced into the reaction chamber, as described above, either before introducing the sample or concomitantly with the sample or after the sample has been introduced into the reaction chamber. However, in a particularly preferred embodiment of the invention, as the case may be, any additional solutions are provided in the reaction chamber before introducing the sample.

Alternatively, introducing the sample to be analyzed, and optionally of further reagents, may also be possible in an indirect manner by means of one or more filling units.

Within the scope of the present invention, a "filling unit" denotes a means for filling the reaction chamber which may be an integrated part of the device of the invention or it may be designed as a separate part that can be attached to the reaction chamber for filling the same and detached after use. Any container that is capable of holding a liquid or gaseous sample to be analyzed in the invention and that can be (reversibly) connected to the reaction chamber may be used as filling unit. A connection between reaction chamber and filling unit may be achieved inter alia by using one or more rigid or flexible tubes, nozzles, cannulae, needles or the like, which may be attached to the reaction chamber and the filling unit, respectively, inter alia by means of press-fit (also referred to as "Luer system") or twist-on fitting (also referred to as "Luer-lock system"), with the latter one being preferred. Both systems are well established in the art and commercially available. A given sample can be introduced into one or more lockable and/or sealable openings of the filling unit in the same way as described above for the direct introduction into the reaction chamber.

In special embodiments, one or more cannulae are used for connecting a filling unit to the reaction chamber of the device. The cannulae used penetrate the lock and/or seal of one or more of the openings comprised in the reaction chamber. Preferred cannulae used in the invention are made of high-grade steel or of synthetic polymers and usually have a diameter of 0.05 mm to 2 mm. Preferably, two cannulae are arranged in such a way that one is used for introducing the sample into the reaction chamber and the other one for taking up excess gaseous material and/or surplus liquids from the reaction chamber (for a detailed description see also the International Patent Application WO 01/02094, whose relevant contents are herewith explicitly referred to).

The filling unit may comprise an integrated or a detachable separate waste container, which serves for taking up surplus gaseous or liquid media from the reaction chamber. Optionally, the waste container comprises with a further gaseous, liquid, or solid filler medium such as inter alia cellulose, filter materials, and silica gels, which binds the liquid or gaseous substances reversibly or irreversibly. Furthermore, the waste container may comprise one or more air vents or may be provided with a vacuum in its interior for improving the transfer of surplus material to the waste container.

The filling unit may further comprise mechanical means ensuring that it accurately fits the respective attachment site of the reaction chamber, i.e. that the filling unit is exactly positioned relative to the reaction chamber to allow connecting the filling unit to the reaction chamber via one or more cannulae, nozzles or the like at preferred sites such as the lockable and/or sealable openings. Examples of such mechanical means include inter alia specifically designed snap fits or spring locks. Preferably, the mechanical means allow detaching the filling unit after introducing the sample and any optional reagents into the reaction chamber.

One advantage of the present invention refers to the fact that sample volumes of 10 µl or less can be analyzed. Typically, sample volumes are in a range of 1 to 1,000 preferably in a range of 1 to 100 µl, more preferably in a range of 1 to 25 µl, and most preferably in a range of 1 to 5 µl.

The samples to be analyzed can be introduced into the reaction chamber without any further purification, since the inventive device and method are specifically designed to allow the detection of analytes in a given sample without the requirement to perform washing and rinsing steps. However, in some cases it might be preferable to purify the sample, at least partially, for example in order to remove any crude contaminations such as solid particles, cell debris or genomic DNA from the sample that would otherwise interfere with the detection of the analytes of interest. Such (partial) purification of the sample can be accomplished in different ways, for example by centrifugation or by filtration of the sample before introducing it into the reaction chamber.

Furthermore, it may be required to dilute a sample to be analyzed due to a comparably high viscosity that would otherwise interfere with the diffusion of the sample through the porous matrix of the inventive device. Dilution of the sample can be easily achieved by adding a diluent to the sample. Examples of suitable diluents include inter alia water, organic and inorganic solvents, phosphate-buffered saline and the like. The diluent may be added before introducing of the sample into the device or may be directly added into the filling unit and/or the reaction chamber, as described above.

In some applications using nucleic acids as analytes, it may also be necessary to amplify the number of analytes present in a given sample, which would otherwise be below the detection limit of the detection method used. Such amplification of one or more species of analytes of interest may, for example, be achieved by performing a polymerase chain reaction (PCR). PCR is an established standard method and is described, e.g., in Sambrook et al., supra; and in Ausubel, F. M. et al., supra. In general, a PCR will be performed before introducing the sample into the inventive device. Alternatively, it may also be possible to perform a PCR directly in a specifically designed filling unit comprising temperature control and/or regulating units enabling the adjustment of specific temperatures required for the denaturation, annealing, and extension steps during a PCR cycle, respectively. Miniaturized PCR devices, i.e. heating and cooling elements as well as temperature sensors and the like, are well known in the art (see, for example, WO 96/10456; WO 96/37303; U.S. Pat. No. 7,030,340; and US 2005/095624). It may also be possible to perform a PCR within the reaction chamber of the inventive device, in particular, if nucleic acid capture molecules are used as primers in the PCR in order to amplify any analyte of interest being present in a given sample.

After the sample, and optionally any additional reagents, have been introduced into the reaction chamber or have been transferred from the one or more filling units into the reaction chamber, the sample is incubated in the reaction chamber for a given period of time. Typically, the incubation period is in the range of 1 s to 30 min, preferably in the range of 1 min to 15 min, and particularly preferably in the range of 1 min to 10 min.

During this incubation period the sample is allowed to diffuse through the porous matrix in the reaction chamber of the device. If the sample is a liquid, the porous matrix becomes preferably soaked by the sample solution and starts swelling. In embodiments of the invention, in which the sample is introduced into the reaction chamber using one or more openings in a lateral sidewall of said chamber, the sample will thus predominantly diffuse—relative to the first surface—laterally through the porous membrane. In a further embodiment of the inventive method, the lateral diffusion of the sample through the porous matrix is accomplished by applying a vectored vacuum to the reaction chamber in parallel to the first surface. The vectored vacuum is applied by connecting a means, preferably a vacuum pump, to the reaction chamber of the device. It is particularly preferred that the means is connected to the lateral sidewall of the reaction chamber that is located opposite to the lateral sidewall, via which the sample has been introduced.

In another preferred embodiment, the analytes present in the sample are allowed to form molecular interactions with the capture molecules immobilized on the porous matrix, while being incubated in the reaction chamber. Finally, these molecular interactions are detected using an appropriate detection method.

In a specific embodiment, the inventive method further comprises immobilizing one or more species of capture molecules on the porous matrix before introducing the sample into the reaction chamber. As already outlined above, depending on the type(s) of capture molecule(s) and the intended application the capture molecules are immobilized on the porous matrix either directly or via a linker molecule by covalent or non-covalent interactions by using standard methods established in the art. In preferred embodiments of the invention, the one or more species of capture molecules are immobilized on the matrix in a site-directed manner. Particularly preferred is an immobilization pattern in which the capture molecules are immobilized in form of "three-dimensional spot", i.e. structures having a substantially column-like shape and passing the porous matrix at least partially in vertical direction relative to the first surface and/or the second surface. Alternatively, the one or more species of capture molecules may also be immobilized on the matrix in an undirected manner, that is without a regular immobilization pattern.

The capture molecules may be immobilized on the porous matrix outside the reaction chamber before placing the same into the reaction chamber. In case the reaction chamber comprises two or more sub-chambers it is also possible to use two or more individual matrices, one for each sub-chamber. Accordingly, it may be possible to immobilize different species of capture molecules on different "sub-matrixes" by treating them independently with one or more species of (different) capture molecules. However, the immobilization of the one or more species of capture molecules may also be performed within the reaction chamber before introducing the sample to be analyzed. For so doing, it is preferred to introduce the capture molecules into the reaction chamber via one or more of the openings preferably in the first surface and/or second surface of the reaction chamber. The capture molecules may be present in a solution of an appropriate volume in order to soak the porous matrix. Typically, the capture molecules may be introduced into the reaction chamber in a liquid volume in the range of 0.001 to 1,000 preferably in the range of 0.05 to 500 more preferably in the range of 0.5 to 200 µl, and most preferably in the range of 1 to 100 µl.

In order to facilitate vertical diffusion of the capture molecules through the porous matrix relative to the first surface, a preferred embodiment of the inventive method comprises applying a vectored vacuum to the reaction chamber perpendicular to the first surface after having introduced the capture molecules. The application of the vectored vacuum is accomplished by connecting a means, preferably a vacuum pump, to the reaction chamber of the device. Preferably, the means is connected to the first surface and or the second surface of the reaction chamber, and particularly preferably it is connected to that surface that is located opposite to the surface via which the capture molecules have been introduced.

After immobilizing the one or more species of capture molecules on the porous membrane any liquid (in which said capture molecules might have been dissolved) may be removed from the matrix either by applying a vectored vacuum, as described above, or in case the matrix is already placed in the reaction chamber by reducing the distance between the first surface and the second surface, thus compressing the matrix and preferably displacing any remaining liquid from the matrix. Preferably, a reduction of the distance between the first surface and the second surface can be achieved by using the above-mentioned one or more means of the inventive device which allow the vertical movement of the first surface and/or the second surface relative to each other. It is particularly preferred to vary the distance between the first surface and the second surface by applying pressure and/or traction to either one or to both of the first surface and/or the second surface via said one or more means.

In another embodiment, the method according to the present invention further comprises introducing one or more agents comprising one or more detectable moieties into the reaction chamber of the device. The term "agent comprising one or more detectable moieties", as used herein, refers to any compound that comprises one or more appropriate chemical substances or enzymes (i.e. one or more "moieties"), which directly or indirectly generate a detectable compound or signal in a chemical, physical or enzymatic reaction. Thus, such an agent may be necessary for or will facilitate detection of one or more analytes of interest by being capable to interact with said analytes. As used herein, the term is to be understood to include both detectable markers as such (also referred to as "labels") as well as any compounds coupled to one or more such detectable markers. In case the one or more species of capture molecules are immobilized on the porous matrix in an undirected manner, for a specific detection taking place different types of detectable markers have to be provided for each type of capture molecule, e.g. detectable markers which differ in their colour.

Detectable markers or labels that may be used according to the invention include any compound which directly or indirectly generates a detectable compound or signal in a chemical, physical or enzymatic reaction. Preferably, the labels can be selected inter alia from enzyme labels, colored labels, fluorescent labels, chromogenic labels, luminescent labels, radioactive labels, haptens, biotin, metal complexes, metals, and colloidal gold. All these types of labels are well established in the art. An example for a physical reaction that is mediated by such labels is the emission of fluorescence or phosphorescence upon irradiation or excitation or the emission of X-rays when using a radioactive label. Alkaline phosphatase, horseradish peroxidase, β-galactosidase, and β-lactamase are examples of enzyme labels, which catalyze the formation of chromogenic reaction products. A particularly preferred enzyme label of the invention is horseradish peroxidase, especially along with using 3,3',5,5'-tetramethylbenzidine as substrate.

In preferred embodiments of the invention, the one or more agents comprising one or more detectable moieties are directly coupled to one or more analytes to be detected. The labeling reaction may be performed outside the inventive device, i.e. before introducing the sample, or directly in the device, optionally in the filling unit already described above. Labeling can be achieved by methods well known in the art (see, for example, Sambrook, J. et al., supra; and Lottspeich, F., and Zorbas H., supra).

For some applications, however, instead of using labeled analytes it might be advantageous to introduce one or more "detection agents" (i.e. agents comprising one or more detectable moieties) separately, that is after having introduced the sample to be analyzed. For example, such an approach may be useful, if a particular label that is directly coupled to an analyte would probably interfere with the binding of the capture molecules (e.g. due to competing binding sites and/or sterical hindrance). The agents comprising one or more detectable moieties may be added anytime during the incubation period and can be introduced into the reaction chamber either directly or via a filling unit, as described above.

In some preferred embodiments of the invention, the one or more agents comprising one or more detectable moieties have binding affinity for one or more analytes to be detected. Examples of such agents include inter alia antibodies as well as fragments thereof (e.g. Fab fragments), antibody-like molecules (e.g. anticalins), and DNA- or RNA-binding proteins as well as fragments thereof. Suitable antibodies or antibody fragments to be used in the invention include both primary antibodies which are raised against the particular analyte to be detected and secondary antibodies which are raised against immunoglobulin G of the animal species in which the primary antibody has been raised. Labeling is accomplished by coupling the agents to one or more detectable markers as described above.

In preferred embodiments of the inventive method, the distance between the first surface and the second surface of the reaction chamber is varied at least in a part of the surface area while the sample to be analyzed is incubated in said reaction chamber. It is particularly preferred that the distance between the first surface and the second surface is reduced. Accordingly, it is within the scope of the present invention either to vary the distance between the first surface and the second surface throughout the entire surface area or to vary the distance in only a part of the surface area such as at one terminal end of the reaction chamber. As already outlined above, a variation of said distance, and thus of the reaction space available, is preferably achieved by using the one or more means which allow the vertical movement of the first surface and/or the second surface relative to each other. These means may be integrated in or attached to the inventive device. A variation of the distance between the first surface and the second surface may be achieved by vertically moving either one of the two surfaces in either direction or by moving both surfaces simultaneously in opposite directions. It is particularly preferred to vary the distance between the first surface and the second surface by applying pressure and/or traction to either one or to both of the first surface and/or the second surface via said one or more means. For example, the distance between the first surface and the second surface can be reduced by moving the first surface vertically towards the second surface, by moving the second surface vertically towards the first surface or by moving both surfaces towards each other. For example, this may be done by taking a device according to the invention in one's hand and applying pressure on the first surface and/or the second surface while holding the device between thumb and forefinger. If the device is integrated into an automated processing system, one or more means such as a stamp or a plunger connected to the reaction chamber may be used to apply pressure on the first surface and/or the second surface.

Reducing the distance between the first surface and the second surface of the reaction chamber results in a concomitant reduction of the reaction space in the chamber as well as in a successive compression of the porous matrix as the distance decreases. Accordingly, the sample to be analyzed, which diffuses through and—in case of a liquid sample—preferably soaks the porous matrix becomes successively displaced from the reaction space as the distance decreases. In a preferred embodiment of the method, the distance between the two surfaces is reduced to such an extent that the sample is substantially displaced from the reaction space. The term "substantially", as used herein, refers to a complete or an almost complete displacement of the sample from the reaction space. Preferably, more than 80%, more preferably more than 90%, and particularly preferably more than 95% of the sample are displaced from the reaction space. Preferably, the sample is transferred to the compensation zones in the reaction chamber, for example by laterally delimiting the reaction chamber by sidewalls made of an elastic material, as described above. By displacing the sample from the reaction space any unbound analytes or labeled detection agents which would otherwise probably interfere with detection and/or causes a high background signal are displaced as well resulting in an increased sensitivity of detection.

When the porous matrix is compressed, the one or more species of capture molecules which are immobilized on said matrix as well as any analytes specifically bound to such a capture molecule are vertically moved towards the first surface and/or the second surface of the reaction chamber as well. If the distance between the two surfaces is reduced to a value close to zero, this means that the capture molecule/analyte complexes are moved into direct proximity to the first surface and/or the second surface, where detection takes place. If the capture molecules are immobilized on the porous matrix in a site-specific manner, preferably in form of "three-dimensional spots", these spots are also compressed as the porous matrix is compressed. Accordingly, the number per unit of volume of any analytes bound to capture molecules immobilized in such manner increases in the compressed state of the matrix. In other words, the three-dimensional spots comprising the capture molecule/analyte complexes are compressed to two-dimensional spots on the respective surface, where detection takes place. This "signal concentration" may also result in higher sensitivity of detection.

After having reduced the distance between the first surface and the second surface it is possible to perform the detection of the analytes bound to the capture molecules on the matrix, as will be described below.

However, at this stage of the method it is preferred to re-increase the distance between the first surface and the second surface of the reaction chamber. It is particularly preferred to restore the original distance, i.e. the distance before the reduction, between the first surface and the second surface of the reaction chamber. This may be achieved by using the means allowing vertical movement of said surfaces, as described above. Re-increasing the distance between the two surfaces results in a concomitant increase in reaction space between the two surfaces. Furthermore, the sample which has been displaced from the reaction space will now diffuse back from the compensation zones to reaction space and thus through the porous matrix. Any analytes of interest, which have not bound to a capture molecule during the first incubation period, now have a further opportunity to form such molecular interactions, which will also improve the sensitivity of the reaction. For example, analytes only being present in a given sample in single or a few copies that have not been in such close proximity with a corresponding capture molecule to bind to it during the first incubation period, may only be detected by such an approach comprising more than one incubation period. During a second or any further incubation period lateral diffusion of the sample through the porous matrix may be facilitated by applying a vectored vacuum parallel to the first surface, as described above.

In a particularly preferred embodiment of the present invention, the subsequent reduction and re-increase of the distance between the first surface and the second surface is repeated at least twice. The number of cycles of reduction and re-increase that can be performed is within the opinion of the practitioner. Typically, the total number of cycles is in a range of 2 to 2,000, preferably in a range of 10 to 1,500, more preferably in a range of 50 to 1,000 and particularly preferably in a range of 100 to 500. In preferred embodiments of the invention, the cycles are performed at a frequency in the range of 1 to 100 cycles per minute. In particularly preferred embodiments of the invention, the frequency is in a range of 20 to 50 cycles per minute.

According to the invention, the detection of the one or more species of the analytes may be performed after each cycle of reducing and re-increasing of the distance between the first surface and the second surface of the reaction chamber. Typically, detection is performed after said distance has been reduced. However, it is also possible to repeat the detection several times, for example after every second or every fifth reduction/re-increase cycle. Furthermore, it is possible to perform the detection only once after the completion of the last reduction/re-increase cycle. In a preferred embodiment, the detection is performed after each reduction/re-increase cycle. The data obtained for a particular analyte in one or more cycles of detection may be analyzed using an appropriated computer software which is known by persons skilled in the art. In each of these embodiments of performing one or more cycles of reducing and re-increasing of the distance between the first surface and the second surface, it is preferred that the detection is performed after the distance between the first surface and the second surface has been reduced, i.e. in the compressed state.

Depending on the particular type of analyte(s) to be detected as well as the nature of detectable markers used detection can be performed by various methods, all of them established in the art (see, for example, Ausubel, F. M. et al., supra; Coligan, J. E. et al. (2000) *Current Protocols in Protein Sciences*, Wiley & Sons, Hoboken, N.J.; and Lottspeich, F., and Zorbas H., supra).

Typically, detecting of the analytes does not require performing any washing or rinsing steps, i.e. no replacement of solutions in the reaction chamber is necessary. Any molecules present in the sample not specifically interacting with the capture molecules immobilized on the porous matrix as well as any unbound detection agents are displaced from the reaction chamber by reducing the distance between the first surface and the second surface.

Thus, performing the method according to the present invention generally involves the use of established and rather simple detection systems, with optical detection systems based on the measurement of parameters such as fluorescence, optical absorption, resonance transfer, and the like being preferred. Particularly preferred are "classical" detection methods based on the measurement of a fluorescent signal such as epifluorescence or darkfield fluorescence microscopy (reviewed, e.g., in: Lakowicz, J. R. (1999) *Principles of Fluorescence Spectroscopy*, $2^{nd}$ ed., Plenum Publishing Corp., NY).

Further fluorescence detection methods that may also be used in the invention include inter alia total internal fluorescence microscopy (see, e.g., Axelrod, D. (1999) *Surface fluorescence microscopy with evanescent illumination*, in: Lacey, A. (ed.) *Light Microscopy in Biology*, Oxford University Press, New York, 399-423), fluorescence lifetime imaging microscopy (see, e.g., Dowling, K. et al. (1999) *J. Mod. Optics* 46, 199-209), fluorescence resonance energy transfer (see, e.g., Periasamy, A. (2001) *J. Biomed. Optics* 6, 287-291), bioluminescence resonance energy transfer (see, e.g., Wilson, T., and Hastings, J. W. (1998) *Annu. Rev. Cell Dev. Biol.* 14, 197-230), and fluorescence correlation spectroscopy (see, e.g., Hess, S. T. et al. (2002) *Biochemistry* 41, 697-705).

Alternatives for the above-mentioned detection systems include white light setups, as described, for example, in WO 00/12759, WO 00/25113, and WO 96/27025; confocal systems, as described, for example, in U.S. Pat. Nos. 5,324,633, 6,027,880, 5,585,639, and WO 00/12759; confocal excitation systems based on Nipkow discs, as described, for example, in U.S. Pat. No. 5,760,950; large-scale integrated fluorescence detection systems using micro-optics, as described, for example, in WO 99/27140; and laser scanning systems, as described, for example, in WO 00/12759. A general description of detection methods using such conventional detection systems can be found, for example, in U.S. Pat. No. 5,324,633.

In addition, electrochemical detection methods may be used, for example by measuring the alteration of redox potentials via electrodes connected to the first surface and/or the second surface (see, e.g., Zhu, X. et al. (2004) *Lab Chip.* 4, 581-587) or by cyclic voltometry (see, e.g., Liu, J. et al. (2005) *Anal. Chem.* 77, 2756-2761; and Wang, J. (2003) *Anal. Chem.* 75, 3941-3945). Furthermore, an electric detection method can be employed, for example by impedance measurement (see, e.g., Radke, S. M. et al. (2005) *Biosens. Bioelectron.* 20, 1662-1667). Detection may also be accomplished by means of detecting acoustic surface waves, as described, e.g., in Z. Guttenberg et al. (2005) *Lab Chip.* 5, 308-317.

In specific embodiments of the present invention, detection of the analytes is performed using FRET or BRET, which are based on the respective formation of fluorescence or bioluminescence quencher pairs, so that a fluorescence signal only occurs, if a target molecule has bound to a capture molecule immobilized on the porous matrix. The use of FRET is also described, e.g., in Liu, B. et al. (2005) *Proc. Natl. Acad. Sci. USA* 102, 589-593; and Szollosi, J. et al. (2002) *J. Biotechnol.* 82, 251-266. The use of BRET is detailed, for example, in Prinz, A. et al. (2006) *Chembiochem.* 7, 1007-1012; and Xu, Y. et al. (1999) *Proc. Natl. Acad. Sci. USA* 96, 151-156;

In a further aspect, the present invention provides a method for the manufacture of a device for the qualitative and/or quantitative detection of analytes, comprising (a) a reaction chamber formed within a chamber body between a first surface and a second surface, wherein the second surface is located opposite to the first surface, and wherein the distance between the first surface and the second surface is variable; and (b) a porous matrix located in the reaction chamber between the first surface and the second surface, wherein the matrix is reversibly compressible, and (c) one or more species of capture molecules which are immobilized on the porous matrix, wherein a vectored vacuum is applied perpendicular to the first surface allowing the vertical diffusion of the one or more species of capture molecules relative to the first surface.

The invention is further described by the following figures and examples, which are solely for the purpose of illustrating specific embodiments of this invention, and are not to be construed as limiting the scope of the invention in any way.

DETAILED DESCRIPTION OF THE FIGURES

FIG. 1 depicts a schematic cross-sectional illustration of an assay device according to the present invention. The reaction chamber of the device is defined by the first surface, the second surface as well as the lateral side walls. The distance between the first surface and the second surface is variable via the means for vertically moving a surface. The reaction chamber is located within a chamber body and optionally sealed. A reversibly compressible matrix is provided within the reaction chamber. An optical detection system is located opposite to the reaction chamber.

Figure 2B:
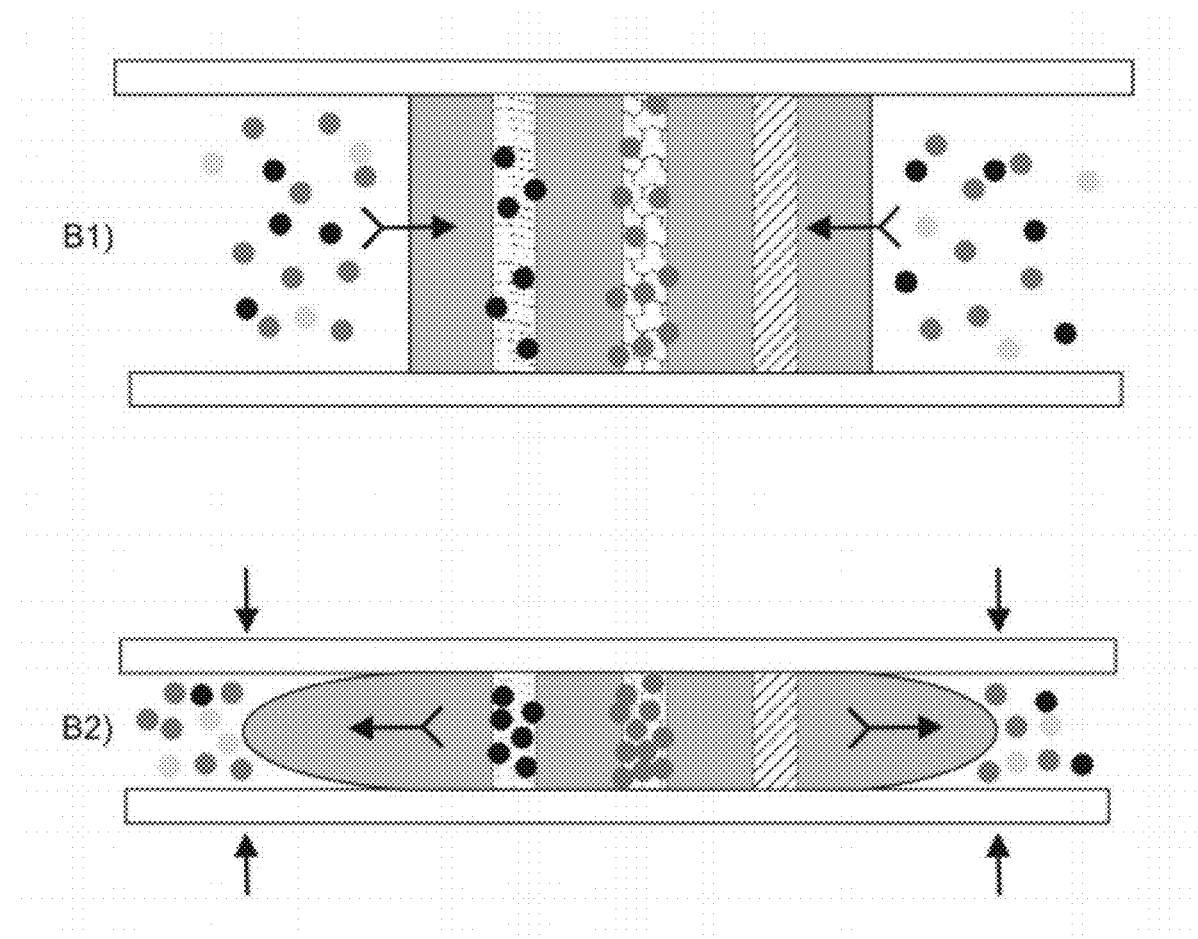
FIG. 2B (B1) illustrates the assay device of FIG. 2A, the capture sites of two of the sets having captured a respective analyte.
Figure 2C:
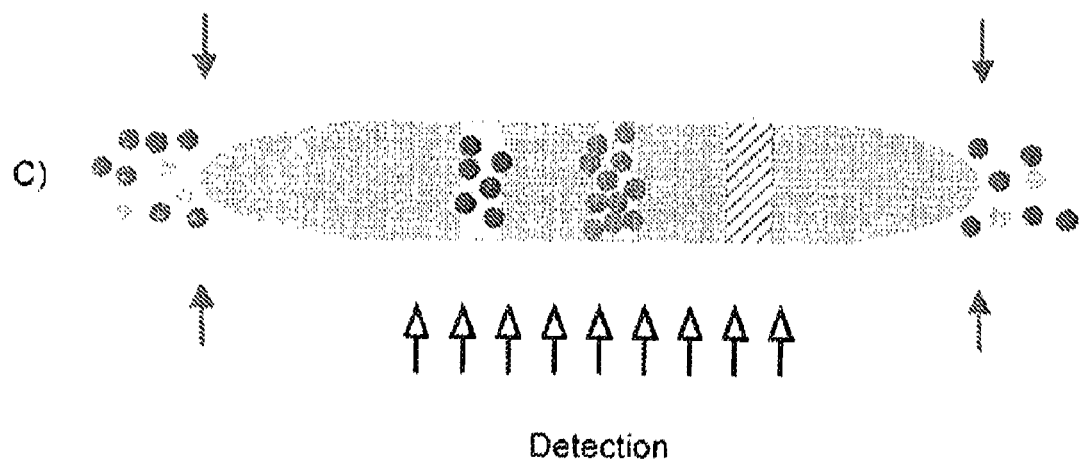
FIG. 2C illustrates detection of captured analyte present in the assay device of FIG. 2B (B2).

FIG. 2 depicts a schematic illustration of a device according to the present invention as well as the method using the same for the qualitative and/or quantitative detection of analytes. (A) The reaction chamber of the device comprises a first surface ("upper surface") and a second surface ("lower surface") as well as a porous matrix ("sponge") located in the reaction chamber between the same, wherein the distance between the first surface and the second surface is variable. Three different species of capture molecules are immobilized on said porous matrix in a site-directed manner, that is in form of "three-dimensional spots" ("spot 1", "spot 2", and "spot 3", respectively). A sample to be analyzed has been introduced into the reaction chamber. The sample comprises two different species of analytes to be detected ("target molecule 1" and "target molecule 2", respectively) as well as molecules having no binding affinity to any of the capture molecules ("no target"). (B1) The sample is incubated in the reaction chamber and meanwhile laterally diffuses through the porous matrix. Lateral diffusion may either be facilitated by (repeatedly) varying the distance between the first surface and the second surface or by applying a vectored vacuum to the reaction chamber in parallel to the first surface. Optionally, one or more agents comprising one or more detectable moieties are introduced into the reaction chamber to facilitate further detection. Preferably, said agents have binding affinity for one or more analytes to be detected. Since target molecule 1 has binding affinity for the particular capture molecule immobilized in spot 1, and target molecule 2 has binding affinity for the capture molecule immobilized in spot 2, respective molecular interactions are formed during this incubation period. (B2) Afterwards, the sample is displaced from the reaction chamber by reducing the distance between the first surface and the second surface. This reduction is accomplished by vertically moving the first surface and/or the second surface towards each other. Concomitantly, the "three-dimensional spots" comprising the analyte/capture molecule complexes are also compressed as the porous matrix is compressed. Accordingly, the number per unit of volume of any analytes bound to capture molecules increases in the compressed state of the matrix. (C) The "concentrated" analyte/capture molecule complexes are detected on the first surface and/or the second surface using a suitable detection system. After having reduced the distance between the first surface and the second surface, however, said distance is preferred to be re-increased. In this case, the displaced sample will diffuse back into the reaction chamber and thus also diffuse again through the porous matrix. Any analytes of interest, which have not bound to a capture molecule during the first incubation period, now have a further opportunity to form molecular interactions with the respective capture molecules in order to improve the sensitivity of the reaction. The subsequent reduction and re-increase of the distance between the first surface and the second surface is repeated at least twice. Preferably, detection is performed after each reduction/re-increase cycle, preferably in the compressed state.

FIG. 3 depicts a polyvinyl acetate (PVA) matrix on which a fluorescent streptavidin-cyanine 5 conjugate has been immobilized. (A) A porous polyvinyl acetate matrix (Bellclean E-1, purchased from Hans J. Michael GmbH, Weissach, Germany) was incubated in 0.12 mM 1,3-diisocyanatohexane (in dimethylformamide, DMF) for 30 min in order to modify its reactive groups, washed in DMF and then in acetonitrile, three times each, and dried under argon. The modified PVA matrix was cut in 3 mm×3 mm pieces, 0.1 µl of 1 mg/ml streptavidin-cyanine5 conjugate (GE Healthcare Life Sciences, Heidelberg) in phosphate buffered saline (PBS) was applied using a pipette, and the matrix was incubated in a drying chamber at 40° C. for 30 min. The immobilization of the conjugate was analyzed using a white light source and a CCD camera (PCO Sensicam, Kehlheim, Germany) with an appropriate filter system. The exposure time was 25 ms. (B) In order to further analyze the size/shape of the immobilized "spot" the PVA matrix was washed in 1 ml PBS for 45 min at 40° C. with agitation (500 rpm). The subsequent detection reaction was performed as described above.

Figure 4:
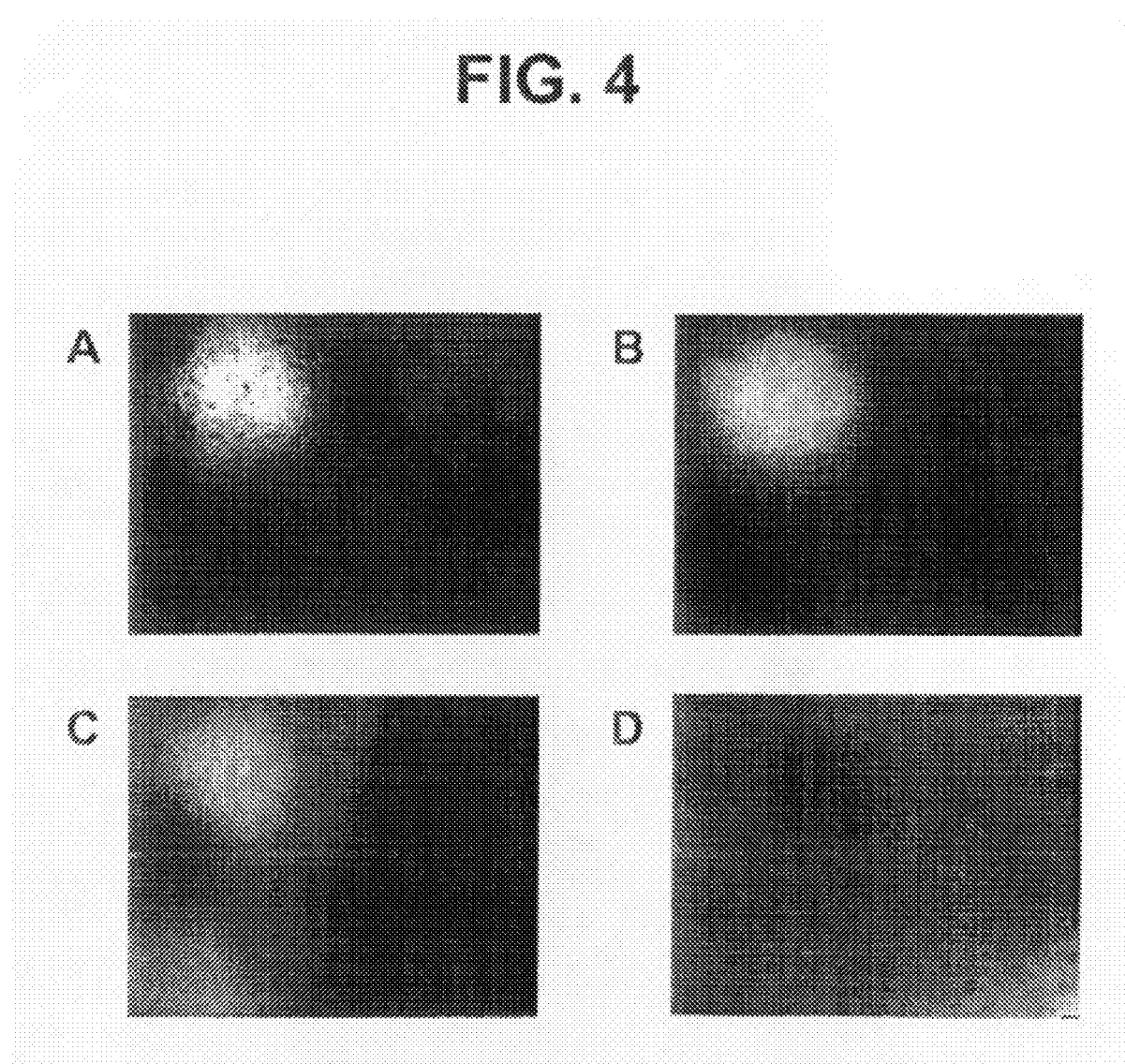
FIG. 4 (A-D) illustrates an assay.

FIG. 4 depicts the results of a qualitative detection assay according to the present invention. A PVA matrix was prepared according to FIG. 3(A). Four different species of capture molecules were immobilized on the matrix by applying 0.1 µl each of the capture molecules on the matrix (respective distance between the spots about 1 mm) and incubating the matrix for 30 min in a drying chamber at 40° C. The following capture molecules were used: 240 µg/ml fuchsine dye (Kremer Pigmente, Aichstätten, Germany) in PBS, pH 7.4 (A); 500 µg/µl streptavidin-cyanine5 conjugate (GE Healthcare Life Sciences, Heidelberg) in PBS (B); 500 µg/ml NT-proBNP antibody 15C4 (Hytest, Turku, Finnland) in PBS (C); and 1% bovine serum albumin in PBS (D) as a negative control. Afterwards, the matrix was placed between two glass slides. Then, the matrix was incubated for 15 min at room temperature with 50 µl of a sample mixture of analytes/detection markers comprising 1 ng/ml NT-proBNP (Hytest, Turku, Finnland), 2 µg/ml streptavidine-phycocrythrin conjugate (GE Healthcare Life Sciences, Heidelberg), and 1 µg/ml biotin-labeled antibody 18C5 (Hytest, Turku, Finnland) in PBS. After applying the sample mixture on the matrix the two glass slides were pressed together several times to facilitate diffusion of the mixture trough the matrix. After the incubation period the two glass slides were pressed together in such way that the sample mixture was substantially displaced from the PVA matrix. The formation of capture molecule/analyte complexes was analyzed using a white light source and a CCD camera (PCO Sensicam, Kehlheim, Germany) with appropriate filter systems. In all cases, the exposure time was 25 ms.

EXAMPLES

Example 1

Modification and Analysis of Porous Matrices

Porous polyvinyl acetate (PVA) matrices (PVA Bellclean E-1 and PVA Bellclean E-2, respectively, both purchased from Hans J. Michael GmbH, Weissach, Germany) having an average pore diameter of about 130 µm were cut in 2.5 cm×2.5 cm pieces. The Bellclean E-1 pieces had a thickness of 1 mm, whereas the Bellclean E-2 pieces had a thickness of 2 mm. The PVA matrices were incubated in 20 ml 0.12 mM 1,3-diisocyanatohexane (in dimethyl formamide, DMF) for 30 min at room temperature with shaking in order to modify their reactive functional groups. Afterwards, they were consecutively washed three times in 20 ml DMF and three times in 20 ml acetonitrile (both obtained from Sigma Aldrich, Munich, Germany) and dried under argon.

In an analogous manner, a viscose sponge having an average pore diameter of about 120 µm (purchased from Siral International, Röttenbach, Germany) was modified. The sponge was cut in cuboids, 1 cm×2 cm×0.5 cm in size. These cuboids were incubated in 20 ml 12 mM 1,3-diisocyanatohexane (in dimethyl formamide, DMF) for 30 min at room temperature with shaking. Subsequent washing steps were performed, as described above.

In order to calculate the internal pore space in the above matrices, i.e. their respective porosity, the "water saturation method" was applied. Thereby, a known volume of the porous material to be analyzed is mixed with a known volume of water. The mixture is incubated for a defined period of time to insure that the material is fully saturated with water. Then, the excess water is removed and its volume measured. The volume of the pore space can now be calculated by subtracting the volume of the unsaturated water from the total volume of water originally used for the analysis. The porosity of the matrix is finally determined by calculating the ratio of the volume of the pore space, as measured above, and the total volume of the matrix and by multiplying the result obtained with 100%.

The respective matrix pieces described above (i.e. pieces having a defined size) were weighed, placed in a petri-dish with a known volume of water and incubated for one hour. After the incubation period, the pieces were weighed again, and the volume of the excess water was measured. Based on the density of water of 1 g/ml, a weight difference of 1 g corresponds to a volume of 1 ml.

Complementary, the swelling behavior of the respective matrices was determined, i.e. their capacity to reversibly bind liquid molecules or to reversibly intercalate them into their structure, this uptake of liquid resulting in an increase of the matrix's total volume. This test was performed by measuring the dimensions of the respective matrix cuboids before and after the incubation period. This ratio provides a measure for the liquid uptake of a material.

The results obtained are summarized in the following table.

| MATRIX TYPE | POROSITY | SWELLING BEHAVIOR |
|---|---|---|
| PVA Bellclean E-1 | 88% | 1.18 |
| PVA Bellclean E-2 | 93% | 1.44 |
| Viscose sponge | 74% | 1.14 |

Example 2

Immobilization of Capture Molecules on the Matrix

A PVA Bellclean-1 matrix according to example 1 was cut in 3 mm×3 mm pieces. Then, 0.1 µl of 1 mg/ml streptavidin-cyanine 5 conjugate (GE Healthcare Life Sciences, Heidelberg) in phosphate buffered saline (PBS; 2.7 mM KCl, 1.5 mM $KH_2PO_4$, 137 mM NaCl, 8.1 mM $Na_2HPO_4$, pH 7.4) were applied to the matrix using a pipette without any further external manipulation. The matrix was incubated at 40° C. for 30 min. Afterwards, the immobilization of the conjugate was analyzed using a white light source an a CCD camera (PCO Sensicam, Kehlheim, Germany). The exposure time was 25 ms (FIG. 3A). A bright signal caused by the cyanine5 fluorophor was observed in a fairly defined region of the matrix.

In order to further analyze the size and/or the shape of this immobilized spot of capture molecules the PVA matrix was washed in 1 ml PBS for 45 min at 40° C. and 500 rpm in a thermomixer device (Eppendorf, Hamburg, Germany). The buffer containing any excess capture molecules was substantially removed by compressing the matrix. Afterwards, the detection reaction was performed as described above (FIG. 3B). It could be observed that the spot has a rather regular, circular shape and that lateral diffusion increases with increasing vertical distance from the application site.

Example 3

Qualitative Detection Assay

A PVA Bellclean-1 matrix was modified according to Example 1. Four different species of capture molecules were immobilized on the matrix by applying 0.1 µl each of the capture molecules on the matrix. The respective capture molecules were applied in a distance from each other of about 1 mm. Subsequently, the matrix was incubated for 30 min in a drying chamber at 40° C.

The following capture molecules were used: 240 µg/ml fuchsine dye (Kremer Pigmente, Aichstätten, Germany) in PBS, pH 7.4 (FIG. 4A); 500 µg/µl streptavidin-cyanine5 conjugate (GE Healthcare Life Sciences, Heidelberg) in PBS (FIG. 4B); 500 µg/ml NT-proBNP antibody 15C4 (Hytest, Turku, Finnland) in PBS (FIG. 4C); and 1% (w/v) bovine serum albumin in PBS (FIG. 4D) as a negative control.

The PVA matrix comprising the different immobilized capture molecules was placed between two glass slides, which constitute the first surface and the second surface of a very simplified reaction chamber. Then, 50 µl of a sample mixture of analytes/detection markers was added to the matrix. This sample mixture comprised 1 ng/ml NT-proBNP (Hytest, Turku, Finnland), 2 µg/ml streptavidine-phycocrythrin conjugate (GE Healthcare Life Sciences, Heidelberg), and 1 µg/ml biotin-labeled antibody 18C5 (Hytest, Turku, Finnland) in PBS. After applying the sample mixture on the matrix the two glass slides were pressed together several times to facilitate diffusion of the mixture trough the matrix. After an incubation period of 15 min at room temperature the two glass slides were pressed together in such way that the sample mixture was substantially displaced from the PVA matrix. The formation of capture molecule/analyte complexes was analyzed in this "compressed state" using a white light source and a CCD camera (PCO Sensicam, Kehlheim, Germany) with appropriate filter systems for the respective fluorophors employed, as described in examples 1 and 2 above. In all cases, the exposure time was 25 ms (FIG. 4A to 4D). In FIG. 4D employing bovine serum albumin as capture molecule, as expected, no signal could be detected. In all other cases, specific capture molecule/analyte complexes could be detected, apparently without any significant signal background.

The present invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The invention claimed is:

1. A method, comprising:
   contacting a set of capture sites comprising multiple capture sites, with a mixture comprising a detectable label and an analyte, the multiple capture sites disposed in a compressible medium in three dimensions and together occupying a total volume, each of the capture sites being capable of capturing the detectable label in the presence of the analyte,
   capturing at least some of the detectable label with respect to each of some of the capture sites,
   decreasing the total volume occupied by the multiple capture sites, and with the multiple capture sites in the decreased volume state, determining the presence of the captured detectable label supported by the compressible medium.

2. The method of claim 1, further comprising, prior to the step of decreasing the total volume occupied by the multiple capture sites, performing a cycle comprising decreasing the total volume occupied by the multiple capture sites and increasing the total volume occupied by the multiple capture sites.

3. The method of claim 2, comprising performing an integer number of cycles, where the integer number of cycles $\geq 1$.

4. The method of claim 1, wherein the mixture comprises a liquid.

5. The method of claim 4, further comprising, prior to the step of determining the presence of the captured detectable label, causing movement of the liquid with respect to the capture sites of the set.

6. The method of claim 5, wherein causing movement of the liquid comprises causing at least some of the liquid to be removed and then to be re-added to the total volume occupied by the capture sites of the set.

7. The method of claim 1, wherein the compressible medium is a porous compressible medium and the step of causing motion comprises moving at least some of the liquid, at least some of the analyte, and at least some of the detectable label within pores of the compressible medium.

8. The method of claim 7, wherein the step of capturing comprises capturing at least some of the detectable label within the pores of the compressible medium.

9. The method of claim 1, wherein the step of decreasing the total volume is performed with the mixture positioned between first and second opposed surfaces and this step comprises reducing a distance separating the first and second opposed surfaces.

10. The method of claim 9, wherein the capture sites of the set of capture sites are supported by a compressible medium and a portion of the compressible medium is secured to one of the first and second opposed surfaces.

11. A device, comprising:
a support member comprising a set of capture sites comprising multiple capture sites, the multiple capture sites disposed in a compressible medium in three dimensions about the member and together occupying a total volume, each of the capture sites capable of capturing a detectable label in the presence of a common analyte, the support member configured to accommodate a liquid mixture in contact with the capture sites, the liquid mixture comprising the detectable label and the analyte,
an actuator configured to decrease the total volume occupied by the capture sites, and a detector configured to determine the presence of captured detectable label attached to the support member when the capture sites are in the decreased-volume state.

12. The device of claim 11, wherein the support member is a porous compressible medium.

13. The device of claim 12, wherein the device is configured to flow at least some of the liquid mixture through pores of the compressible medium.

14. The device of claim 13, wherein the device is configured to cause at least some of the liquid mixture to re-enter pores of the compressible medium after exiting pores of the compressible medium.

15. The device of claim 11, wherein the support member is positioned between first and second surfaces impermeable to the liquid and at least some of the liquid mixture is displaced from between the surfaces when the actuator decreases the total volume occupied by the capture sites.

16. The device of claim 15, further comprising a reservoir configured to receive displaced liquid.

17. The device of claim 11, further comprising a processor configured to operate the actuator and detector and to determine the presence of the analyte based on the presence of the captured detectable label.

* * * * *